United States Patent [19]

Nobel et al.

[11] Patent Number: 5,625,094
[45] Date of Patent: Apr. 29, 1997

[54] RHODIUM/IRIDIUM CATALYZED SYNTHESIS OF CARBOXYLIC ACIDS OR ESTERS THEREOF

[75] Inventors: Dominique Nobel, Fontaines/Saint/Martin; Robert Perron, Charly; Philippe Denis, Decines, all of France

[73] Assignee: Rhone-Poulenc Chimie, Courbevoie Cedex, France

[21] Appl. No.: 450,137

[22] Filed: May 26, 1995

Related U.S. Application Data

[63] Continuation of Ser. No. 221,233, Mar. 31, 1994, abandoned.

[30] Foreign Application Priority Data

Mar. 31, 1993 [FR] France ............................... 93 03733

[51] Int. Cl.$^6$ ............................................. C07C 67/36
[52] U.S. Cl. ......................... 560/232; 562/517; 562/519; 562/520
[58] Field of Search ...................... 560/232; 562/517, 562/519, 520

[56] References Cited

U.S. PATENT DOCUMENTS

| | | | |
|---|---|---|---|
| 3,769,329 | 10/1973 | Paulik et al. | 260/488 |
| 3,772,380 | 11/1973 | Paulik et al. | 260/488 |
| 3,845,121 | 10/1974 | Eubanks et al. | 260/532 |
| 3,852,346 | 12/1974 | Forster et al. | 260/546 |
| 5,001,259 | 3/1991 | Smith et al. | 562/519 |
| 5,237,097 | 8/1993 | Smith et al. | 562/519 |

FOREIGN PATENT DOCUMENTS

| | | |
|---|---|---|
| 0616997A1 | 9/1994 | European Pat. Off. . |
| 2317269 | 2/1977 | France . |
| 2142012 | 1/1985 | United Kingdom . |

OTHER PUBLICATIONS

Patent Abstracts of Japan, vol. 9, No. 96, (C–278) [1819], Apr. 25, 1985 & JP–A–59 227 832 (Kogyo Gijutsuin et al.), Dec. 21, 1984.

Patent Abstracts of Japan, vol. 9, No. 96, (C–278) [1819], Apr. 25, 1985, & JP–A–59 227 831 (Kogyo Gijutsuin et al.), Dec. 21, 1984.

Patent Abstracts of Japan, vol. 9, No. 222, (C–302) [1945], Sep. 9, 1985, & JP–A–60–084 234 (Kogyo Gijutsuin et al.), May 13, 1985.

*Primary Examiner*—Porfirio Nazario-Gonzalez
*Assistant Examiner*—Rosalyne Williams
*Attorney, Agent, or Firm*—Burns, Doane, Swecker & Mathis, L.L.P.

[57] ABSTRACT

Process for the preparation of a carboxylic acid or ester thereof. The process includes reacting at least one alcohol, alkyl or aryl halide, ether or ester, with carbon monoxide, in the presence of a catalytically effective amount of at least one rhodium compound or rhodium metal, at least one iridium compound or iridium metal, or at least one mixed rhodium/iridium compound, and at least one halogen-containing promoter therefor.

29 Claims, No Drawings

RHODIUM/IRIDIUM CATALYZED SYNTHESIS OF CARBOXYLIC ACIDS OR ESTERS THEREOF

This application is a continuation of application Ser. No. 08/221,223, abandoned.

BACKGROUND OF THE INVENTION

1. Field of the Invention

The present invention relates to a process for the preparation of carboxylic acids comprising (n+1) carbon atoms, by reaction of carbon monoxide with at least one carbonylable compound having (n) carbon atoms, in the presence of a homogeneous catalyst based on rhodium and iridium.

2. Description of the Prior Art

The preparation of carboxylic acids, and more particularly of acetic acid, by reaction of an alcohol, such as methanol, with carbon monoxide is a well-known process which has been exploited industrially, and has been the subject of numerous articles and patents, such as, for example, U.S. Pat. Nos. 3,769,329 and 3,813,428. The processes described in these references use a catalytic system based on rhodium and a halogen-containing compound.

Such processes are commonly exploited in installations consisting of a reaction area comprising a reactor under pressure and an area for separation of the acid formed from the rest of the reaction mixture; the separation being achieved by partial evaporation of the mixture. The evaporated part, mainly comprising the acid product, is subsequently sent to a purification area, consisting of several distillation columns; the other part, in particular comprising the catalytic system, remains in liquid form and is recycled to the reactor.

Despite their recognized performances, these modes of preparation have, however, serious constraints in the conduct of the reaction. These are mainly due to the nature of the catalyst used, and more particularly to the nature of the metal element of the catalytic system. As indicated above, the metal used industrially in the reaction for the carbonylation of methanol is rhodium. In liquid phase reactions, the latter typically takes the form of a soluble rhodium complex for which the ligands are carbon monoxide and iodine.

However, it is now recognized that such catalysts are extremely sensitive to variations in the composition of the reaction medium, such as in particular the water content, or alternatively the partial pressure of carbon monoxide. A reduction in the content of one of these constituents or of them both, in the reaction medium, may be the cause of a loss of rhodium in the form of an insoluble and inactive precipitate, consequently resulting in a reduction in the production efficiency.

The critical area of the process regarding the carbon monoxide deficiency lies in the area of separation where the reaction mixture is partially evaporated under the effect of a pressure reduction.

The partial pressure of CO is then considerably diminished, resulting in irreversible losses of precious metal.

Several solutions have been recommended to compensate for the effect of the carbon monoxide deficiency. An obvious solution is the addition of supplementary rhodium, but such a means is not economically viable.

Other more satisfying means have been proposed, such as, for example, an increase in water content, or the addition of stabilizing agents to the reaction medium. In particular, Patent Application EP 55,618 describes the use of such compounds. The latter may be chosen from organic species such as N,N,N,N'-tetramethyl-o-phenylenediamine, disubstituted phosphines such as bis(diphenylphosphino) methane, bis(di-p-tolylphosphino)methane, polyacids such as citric acid or succinic acid, or alternatively from inorganic compounds based on germanium, antimony or tin, or alkali metals in the form of halides, acetate or alternatively oxides.

As regards the water content in the medium, it has an influence on the installation as a whole and not only in the areas where the catalyst is present.

In fact, water has a recognized beneficial action on the stability of rhodium, but also on the rate of carbonylation, and thus on the production efficiency of the installation. This is why the first processes developed use reaction compositions having very high water contents, of the order of 14% to 20% in general, relative to the total weight of the mixture. However, the presence of such water contents in the area of separation and of purification of the acid formed is restricting in the sense that it represents a considerable amount of energy consumed in order to obtain a sufficient dehydration of the acid.

In view of the above, two opposing interests are found. The first interest is connected to the requirement to conserve the catalyst in a form which is soluble in the medium in order to have a good production efficiency for the reaction, thus to increase the amount of water. The second interest tends towards decreasing the latter in order to minimize the cost of the subsequent separation of the acid formed from the water present.

New processes have appeared which offer a compromise between the contradictory interests indicated.

Patent Application EP 161,874 describes a process for the carbonylation of methanol to acetic acid, using the usual catalytic system. The innovation provided consists in maintaining the constituents of the reaction mixture, which are precisely defined, in very specific proportions during the course of the carbonylation. The process is carried out in the presence of a water content which is lower than 14% and may also be as low as 1%, and moreover requires the use of considerable amounts, up to 20%, of a soluble iodide salt which stabilizes the rhodium, preferably lithium iodide.

SUMMARY OF THE INVENTION

The subject of the present invention is a process, in the liquid phase, for the preparation of carboxylic acids which uses a catalytic system based on rhodium and iridium. The process according to the invention makes it possible to operate in an extended range of water contents in the reaction mixture without a loss of precious metals by precipitation being observed at low water contents. In addition, the process according to the invention makes it possible to achieve production efficiencies which are comparable with those of the standard processes.

In addition, and this represents a totally unexpected advantage, the results mentioned above may be obtained without it being necessary to use considerable amounts of additives for stabilizing the catalyst. It has even been observed that the process according to the invention could be implemented efficiently without having to use such compounds.

DETAILED DESCRIPTION OF THE PREFERRED EMBODIMENTS

The process according to the invention relates to the production of carboxylic acids comprising (n+1) carbon atoms, or corresponding esters, by bringing carbon monoxide in the reaction mixture together with at least one reactant chosen from the compounds of formulae:

$$R(OH)_m \quad (1);$$

$$RX \quad (2);$$

$$ROR' \quad (3);$$

$$ROCOR' \quad (4);$$

in which formulae R and R', which may be identical or different, each represent a $C_1-C_{10}$ hydrocarbon radical, R having n carbon atoms; X represents chlorine, bromine or iodine and m is 1 or 2, the reaction being carried out the in the presence of a catalytic system comprising at least one rhodium compound, at least one iridium compound or at least one compound containing these two metals, and at least one halogen-containing promoter.

As has been indicated above, the present invention is carried out with a catalytic system based on two metals: rhodium and iridium.

The combination of these two elements provides two advantages relative to a process which only uses a single metal.

It has in fact been found that the simultaneous use of rhodium and iridium as metal constituents of the catalytic system made it possible to increase the rate of carbonylation in a totally unexpected manner. Expressed differently, the process according to the invention makes it possible to achieve a rate of carbonylation, expressed in moles, at least equal to that obtained with a catalytic system which only employs a single metal, under the same conditions, whereas the total number of moles of metals used in the process of the invention is lower.

Besides increasing the production efficiency, the fact of obtaining comparable rates while employing a lower number of moles of catalyst constitutes an additional advantage, in terms of economy: that of decreasing the costs of the catalyst.

Moreover, the process according to the invention makes it possible to efficiently carry out the carbonylation reaction with water contents in the medium which are lower than those used in the standard processes, without it being necessary to add to the medium the considerable amounts of catalyst stabilizer required in the prior art. As has been indicated above, the process according to the invention may be implemented even in the absence of such compounds.

However, other advantages will become clearer on reading the description which will follow.

The reaction according to the invention is carried out in the liquid phase; as a consequence, the catalytic system used is in a form which is soluble in the reaction medium.

The catalytic system suitable for carrying out the invention is based on at least one rhodium compound, at least one iridium compound and at least one halogen-containing promoter.

The compounds based on rhodium and iridium commonly used in carbonylation reactions may be used in the process according to the invention.

The compounds used based on rhodium and iridium are generally chosen from coordination complexes of these metals, which are soluble in the medium under the reaction conditions. More particularly, coordination complexes are used for which the ligands are, on the one hand, carbon monoxide and, on the other hand, a halogen such as chlorine, bromine or more particularly iodine. Of course, the use of soluble complexes comprising ligands other than those mentioned, such as in particular organophosphorus or nitrogen-containing ligands, would not be departing from the scope of the present invention. Advantageously, however, the present invention does not require the use of complexes of rhodium and of iridium of this type.

Thus, by way of examples of coordination complexes more particularly used in the present invention, there may especially be mentioned complexes of the type $Ir_4(CO)_{12}$, $Ir(CO)_2I_2^-Q^+$, $Ir(CO)_2Br_2^-Q^+$, $Rh_4(CO)_{12}$, $Rh(CO)_2I_2^-Q^+$, $Rh(CO)_2Br_2^-Q^+$, or alternatively complexes based on the two metals such as $Rh_3Ir(CO)_{12}$, $Rh_2Ir_2(CO)_{12}$; in which formulae Q may especially represent hydrogen, the group $NR_4$ or $PR_4$, with R chosen from hydrogen and a hydrocarbon radical.

Compounds chosen from simple salts of these elements may equally be used in the process according to the invention, such as in particular $IrI_3$, $IrBr_3$, $IrCl_3$, $IrI_3.4H_2O$, $IrBr_3.4H_2O$, $RhI_3$, $RhBr_3$, $RhCl_3$, $RhI_3.4H_2O$, $RhBr_3.4H_2O$, or alternatively rhodium and iridium in the metal state.

It should be noted that this above-mentioned list of compounds based on rhodium and iridium cannot be considered as exhaustive, and that, by way of additional examples of compounds of the two metals mentioned above, reference may be made to U.S. Pat. Nos. 3,769,329 and 3,772,380, the teaching of which are hereby incorporated by reference.

The proportion of one metal relative to the other may vary within wide limits. The rhodium/iridium atomic ratio in the catalytic system according to the invention is between 0.01 or higher.

The total metal concentration in the reaction medium is generally between 0.1 and 100 mmol/l, preferably between 1 and 10 mmol/l.

Besides the abovementioned compounds based on rhodium and iridium, the catalytic system according to the invention comprises a halogen-containing promoter. The latter may take the form of a halogen by itself, or in combination with other elements such as, for example, hydrogen, a $C_1-C_{10}$ alkyl radical, a $C_1-C_{10}$ acyl radical, or alternatively a $C_6-C_{10}$ aryl radical The halogen is in general chosen from chlorine, bromine or iodine, iodine being preferred.

According to a particular embodiment of the invention, the promoter used comprises hydrogen or a $C_1-C_{10}$ alkyl radical. More particularly, the promoter used in the invention comprises the halogen and a $C_1-C_{10}$ alkyl radical.

The abovementioned radical of the halogen-containing promoter preferably corresponds to the hydrocarbon radical of the reactant which is carbonylated during the reaction according to the invention.

By way of halogen-containing compounds which are capable of being used as promoters, there may be mentioned iodine, hydriodic acid, hydrobromic acid, methyl iodide, methyl bromide, ethyl iodide, 1,1-diiodoethane, benzyl bromide or acetyl iodide.

According to a variant of the invention, the halogen-containing promoter is introduced into the reaction mixture, in part or in total, in the form of a precursor. In such a case, the said precursor generally takes the form of a compound which is capable of releasing the hydrocarbon radical of the abovementioned halogen-containing promoter into the reaction medium, under the action of a halogen or in particular of the hydrohalic acid, these latter compounds being present in the medium or else introduced with this aim.

By way of non-limiting examples of suitable precursors, there may be mentioned the compounds chosen from alcohols of formula (1) ROH, ethers of formula (2) ROR' or alternatively esters of formula (3) R'COOR, used alone or mixed. In the abovementioned formulae, the radicals R and R', which may be identical or different, each represent a $C_1$–$C_{10}$ saturated or $C_6$–$C_{10}$ aromatic hydrocarbon radical; the radical R corresponding to the radical of the halogen-containing promoter.

Thus, methanol, ethanol, propanol, butanol, dimethyl ether and methyl acetate are suitable precursors for the said halogen-containing promoter.

The amount of halogen-containing promoter present in the reaction mixture is between 0 (exclusively) and 20% relative to the total weight of the said mixture. The content of halogen-containing promoter is preferably between 0 (exclusively) and 15%.

It should be noted that, if the abovementioned promoter is introduced, in part or in total, in the form of a precursor, the amount of precursor or of promoter/precursor mixture is such that it makes it possible to obtain an equivalent amount to that mentioned above.

The preparation of carboxylic acids or corresponding esters according to the invention is carried out starting from a reactant which has one carbon atom less relative to the final acid or ester product. This reactant is chosen from the following compounds, alone or mixed:

$$R(OH)_m \quad (1);$$
$$RX \quad (2);$$
$$ROR' \quad (3);$$
$$ROCOR' \quad (4);$$

in which formulae R and R', which may be identical or different, each represent a $C_1$–$C_{10}$ hydrocarbon radical, R having n carbon atoms; X represents chlorine, bromine or iodine and m is 1 or 2.

Thus, the carbonylation reaction according to the invention may in particular be carried out in the presence of methanol, ethanol, propanol, ethylene glycol, 1,4-butanediol, methyl iodide, methyl bromide, ethyl iodide, 1,1-diiodoethane, ethylene oxide, methyl acetate, ethyl acetate or acetyl iodide.

According to a preferred embodiment of the invention, the reactant employed in the process is chosen from monohydroxylated alcohols and alkyl halides.

The reactant content in the reaction mixture is between 0 (exclusively) and 40% by weight relative to the total weight of the medium. The said reactant content is preferably between 0 (exclusively) and 30%.

The other reactant necessary for obtaining a carboxylic acid is carbon monoxide. This may be used in pure form or diluted in gases such as hydrogen, methane, carbon dioxide or any other type of gas such as, for example, nitrogen.

According to a particular embodiment of the invention, carbon monoxide which is at least 99% pure is used.

The partial pressure of carbon monoxide usually varies between 10 and 50 bars, preferably between 10 and 20 bars.

The carbonylation reaction according to the invention is in addition carried out in the presence of water. Thus, as has been indicated beforehand, the process according to the invention makes it possible to obtain a good production efficiency at low water contents, without loss of catalytic metal by precipitation.

Thus, the process which is the subject of the invention may be carried out in a wide range of water concentration in the reaction medium, equivalent to between 0 (exclusively) and 14% relative to the total weight of the said medium. The water content in the reaction medium is more particularly between 0 (exclusively) and 10%.

One of the remarkable advantages of the present invention, as indicated beforehand, resides in the fact that it is possible to carry out the carbonylation reaction, if not in the absence of soluble iodide salts, at least only using them in low amounts.

Thus, the content of soluble iodide salts present in the reaction medium is between 0 and 5% by weight relative to the total weight of the said mixture. It is recalled here that the soluble salts are chosen from standard organic or inorganic compounds and more particularly from alkali metal or alkaline-earth metal iodides. This content is preferably between 0 and 2%.

Besides the abovementioned compounds and reactants, the carbonylation reaction according to the invention is carried out in the presence of esters.

The ester used preferably corresponds to the reaction of the acid formed with the alcohol present in the medium, as it is if used as a reactant, or in a masked form if the reactant used is a halide, an ether or an ester.

According to one embodiment of the invention, the ester content is between 0 (exclusively) and 40% by weight relative to the weight of the reaction mixture. This content more particularly varies between 0 (exclusively) and 30%.

Finally, the carbonylation reaction is carried out in the presence of a solvent. The solvent used in the process according to the invention is advantageously the carboxylic acid or the ester formed. Of course, other solvents may be used, such as in particular compounds which ale inert towards the reaction mixture and which have a boiling point higher than that of the acid formed, such as for example benzene.

Commonly, the carbonylation reaction is carried out at a temperature between 150° and 250° C.

The total pressure is generally between 5 and 200 bars, and preferably between 5 and 100 bars.

Of course, the process according to the invention may be implemented in a continuous or batchwise fashion.

In the case where the process is implemented in continuous fashion, the contents of the various components of the reaction mixture, corresponding to the stable operating conditions of the process, are within the concentration ranges given above and are maintained as such during the course of the reaction.

During the start of the reaction, the various components are introduced into a suitable reactor, fitted with stirring means which are sufficient to provide the gas-liquid transfer. It should be noted that, if the reactor preferably comprises means for mechanical stirring of the reaction mixture, operation without such means is not excluded, the homogenization of the mixture being achieved by the introduction of carbon monoxide into the reactor.

The components of the reaction mixture are introduced without any preferred order, in their own form and/or in the form of one or more precursors.

It should be noted that this process according to the invention may be implemented industrially in existing installations which utilize a catalyst based on rhodium.

The process according to the invention is suitable for the manufacture of all types of carboxylic acids or corresponding esters comprising at least two carbon atoms. Thus, the said process may be implemented in order to prepare propionic acid from ethanol, succinic acid from ethylene oxide, or adipic acid from 1,4-butanediol.

However, this process is very particularly suitable for obtaining acetic acid or methyl acetate, in particular from methanol, in the presence of methyl acetate, water and methyl iodide as the halogen-containing promoter.

Concrete but non-limiting examples of the invention will now be presented.

EXAMPLE 1

The aim of this example is to illustrate the synergy created during the use of rhodium and iridium relative to the use of catalysts based on one or other of the metals.

The procedure is as follows:

There are successively introduced into a glass bulb:

16.5 g of acetic acid;
2.3 g of methyl iodide;
0.5 g of methyl acetate;
1.3 g of methanol;
1.9 g of water.

The catalyst is introduced before the abovementioned components, in the form of a solution of rhodium iodide and/or iridium chloride in acetic acid. Thus, the rhodium and iridium solutions used respectively contain 1.5% and 1.75% of metal in acetic acid.

The amount of rhodium and/or iridium is, moreover, adjusted so that the total metal concentration is 4 mmol/l.

Once the constituents have been charged, the bulb is placed in an autoclave, itself placed in an oven incorporating agitation and connected to the CO supply under pressure.

The autoclave, under an initial pressure of 5 bars, is brought to a temperature of 185° C. and the total pressure is regulated at 30 bars.

The autoclave is cooled when approximately 2% of methyl acetate remains in the reaction medium.

The results obtained are assembled in the table below:

TABLE 1

| TESTS | Rh/Ir PROPORTION (%/%) | $R_{CARB}$ (mol/h · l) |
|---|---|---|
| A | 100/0 | 6 |
| B | 75/25 | 7.5 |
| C | 50/50 | 6 |
| D | 25/75 | 6 |
| E | 0/100 | 4 |

$R_{CARB}$ represents the rate of carbonylation

The percentages indicated are expressed in moles.

This table clearly shows that the rate of carbonylation of methanol in the presence of the two metals is always greater than or equal to that obtained when only one metal is used at a time, under conditions where the water content is approximately 10% by weight of the total reaction mixture and the methyl iodide content approximately 9% by weight.

EXAMPLE 2

The aim of this example is to illustrate the synergy created during the use of rhodium and iridium relative to the use of catalysts based on one or other of the metals, under conditions which are different from those of Example 1.

There are successively introduced into a glass bulb:

19.6 g of acetic acid;
1.15 g of methyl iodide;
0.5 g of methyl acetate;
1.3 g of methanol;
0.5 g of water.

The catalyst is introduced before the abovementioned components, in the form of a solution of metal in acetic acid for both of the said metals.

The rhodium and iridium solutions used are the same as those of Example 1.

The amount of rhodium and/or iridium is in addition adjusted so that the total metal concentration is 4 mmol/l.

The procedure is carried out according to the method described in Example 1. The results obtained are assembled in the table below:

TABLE 2

| TESTS | Rh/Ir PROPORTION (%/%) | $R_{CARB}$ (mol/h · l) |
|---|---|---|
| A | 100/0 | 2.2 |
| B | 75/25 | 7.5 |
| C | 50/50 | 3.5 |
| D | 25/75 | 3.6 |
| E | 0/100 | 3 |

The rates of carbonylation obtained still show the synergy effects of the two metals simultaneously during the reaction, under conditions where the water content is approximately 5% by weight (relative to the total weight of the mixture) and the methyl iodide content is approximately 5% by weight.

EXAMPLE 3

The tests which follow were carried in continuous fashion in an autoclave fitted with means for introducing the reactants necessary to the reaction. The reaction solution contains on average 5.5 mmol/l of rhodium and of iridium.

The residence time in the reactor is approximately 10 minutes.

The mixture exiting the autoclave is degassed and cooled.

The composition of the reaction mixture is analysed by gas phase chromatography.

The total pressure in the autoclave is 30 bars and the temperature is maintained at 190° C.

The procedure is carried out such that the composition of the reaction mixture is maintained as indicated in Table 3.

The rate of carbonylation is obtained by measurement of the rate of consumption of the CO, account in addition being taken of the amount of CO involved in the formation of carbon dioxide.

TABLE 3

| TESTS | $H_2O$ | $CH_3OH$ | $CH_3CO_2CH_3$ | $CH_3I$ | $CH_3CO_2H$ | Rh/Ir | $R_{CARB}$ |
|---|---|---|---|---|---|---|---|
| A | 4.6 | 0.12 | 8.7 | 15 | 70 | 44/55 | 11.1 |
| B | 5.6 | 0.3 | 13 | 14.6 | 65 | 44/55 | 12.8 |
| C | 6.6 | 0.5 | 16.3 | 12.4 | 63 | 44/55 | 13.7 |

In this table, the contents indicated for the various constituents of the mixture are expressed by weight relative to the total weight of the mixture, and the rate of carbonylation is expressed in mol/h.l of acetic acid formed.

We claim:

1. A process for the preparation of a carboxylic acid or ester thereof, comprising reacting at least one alcohol, alkyl or aryl halide, ether or ester, with carbon monoxide in the presence of a catalytically effective amount of at least one rhodium compound or rhodium metal and at least one iridium compound or iridium metal, or at least one mixed rhodium/iridium compound; and at least one halogen-containing promoter therefor.

2. The process as defined by claim 1, comprising reacting at least one alcohol having the formula $R(OH)_m$, in which R is a $C_1$–$C_{10}$ hydrocarbon radical and m is 1 or 2, with said carbon monoxide.

3. The process as defined by claim 1, comprising reacting at least one alkyl or aryl halide having the formula RX, in which R is a $C_1$–$C_{10}$ hydrocarbon radical and X is chlorine, brownine or iodine, with said carbon monoxide.

4. The process as defined by claim 1, comprising reacting at least one ether having the formula ROR', in which R and R' are each a $C_1$–$C_{10}$ hydrocarbon radical, with said carbon monoxide.

5. The process as defined by claim 1, comprising reacting at least one ester having the formula ROCOR', in which R and R' are each a $C_1$–$C_{10}$ hydrocarbon radical, with said carbon monoxide.

6. The process as defined by claim 1, wherein the atomic ratio of rhodium to iridium values 0.01 or higher.

7. The process as defined by claim 1, the total concentration of rhodium and iridium values in the medium of reaction ranging from 0.1 to 100 mmol/l.

8. The process as defined by claim 7, said total concentration ranging from 1 to 10 mmol/l.

9. The process as defined by claim 1, carried out in liquid phase.

10. The process as defined by claim 9, carried out in the presence of water.

11. The process as defined by claim 10, the medium of reaction comprising up to 14% by weight of water.

12. The process as defined by claim 11, the medium of reaction comprising up to 10% by weight of water.

13. The process as defined by claim 1, said at least one halogen-containing promoter comprising a hydrogen atom or a $C_1$–$C_{10}$ alkyl or acyl, or a $C_6$–$C_{10}$ aryl radical.

14. The process as defined by claim 1, the medium of reaction comprising up to 20% by weight of said at least one halogen-containing promoter.

15. The process as defined by claim 14, the medium of reaction comprising up to 15% by weight of said at least one halogen-containing promoter.

16. The process as defined by claim 1, the medium of reaction comprising up to 40% by weight of said at least one alcohol, halide, ether or ester.

17. The process as defined by claim 16, the medium of reaction comprising up to 30% by weight of said at least one alcohol, halide, ether or ester.

18. The process as defined by claim 1, carried out in the presence of coordination complexes of rhodium and iridium which are soluble in the medium reaction.

19. The process as defined by claim 1, said at least one halogen-containing promoter comprising iodine, hydriodic acid, hydrobromic acid, methyl iodide, methyl bromide, ethyl iodide, 1,1-diiodoethane, benzyl bromide or acetyl iodide.

20. The process as defined by claim 1, carried out in the presence of no greater than 5% by weight of a soluble iodine salt.

21. The process as defined by claim 9, said catalyst compounds and promoter therefor being soluble in the medium of reaction.

22. The process as defined by claim 1, said at least one halogen-containing promoter corresponding to an organic radical comprising said alcohol, alkyl or acyl halide, ether or ester.

23. The process as defined by claim 1, comprising reacting methanol, ethanol, propanol, ethylene glycol, 1,4-butanediol, methyl iodide, methyl bromide, ethyl iodide, 1,1-diiodoethane, ethylene oxide, methyl acetate, ethyl acetate or acetyl iodide with said carbon monoxide.

24. The process as defined by claim 1, carried out in the presence of a carboxylic acid ester.

25. The process as defined by claim 1, carried out in the presence of a carboxylic acid.

26. The process as defined by claim 1 for the preparation of propionic acid, comprising reacting ethanol with said carbon monoxide.

27. The process as defined by claim 1 for the preparation of succinic acid, comprising reacting ethylene oxide with said carbon monoxide.

28. The process as defined by claim 1 for the preparation of adipic acid, comprising reacting 1,4-butanediol with said carbon monoxide.

29. The process as defined by claim 1, comprising reacting methanol with said carbon monoxide, in the presence of methyl iodide, methyl acetate and water, in an acetic acid reaction solvent.

* * * * *